(12) United States Patent
Khosla et al.

(10) Patent No.: US 10,024,776 B2
(45) Date of Patent: Jul. 17, 2018

(54) APPARATUS FOR IN-LINE TESTING AND SURFACE ANALYSIS ON A MECHANICAL PROPERTY TESTER

(71) Applicants: Vishal Khosla, San Jose, CA (US); Nick Doe, San Jose, CA (US); Jun Xiao, San Jose, CA (US); Ming Chan, San Jose, CA (US); Gautam Char, San Jose, CA (US)

(72) Inventors: Vishal Khosla, San Jose, CA (US); Nick Doe, San Jose, CA (US); Jun Xiao, San Jose, CA (US); Ming Chan, San Jose, CA (US); Gautam Char, San Jose, CA (US)

(73) Assignee: RTEC-INSTRUMENTS, INC., San Jose, CA (US)

( * ) Notice: Subject to any disclaimer, the term of this patent is extended or adjusted under 35 U.S.C. 154(b) by 26 days.

(21) Appl. No.: 15/214,623

(22) Filed: Jul. 20, 2016

(65) Prior Publication Data

US 2018/0024035 A1    Jan. 25, 2018

(51) Int. Cl.
*G01B 9/02* (2006.01)
*G01N 3/56* (2006.01)

(52) U.S. Cl.
CPC ........ *G01N 3/56* (2013.01); *G01B 9/02* (2013.01)

(58) Field of Classification Search
CPC .............. G01B 9/02027; G01B 9/0209; G01B 11/2441; G01N 23/2204; G01N 23/225; H01J 2237/2817; H01J 2237/202; H01J 37/285

See application file for complete search history.

(56) References Cited

U.S. PATENT DOCUMENTS

| 3,147,017 | A | | 9/1964 | Dunham | |
|---|---|---|---|---|---|
| 4,451,197 | A | | 5/1984 | Lange | |
| 5,852,232 | A | * | 12/1998 | Samsavar | G01B 17/00 73/105 |
| 6,015,174 | A | | 1/2000 | Raes et al. | |
| 6,057,547 | A | * | 5/2000 | Park | B82Y 35/00 850/10 |
| 6,272,907 | B1 | * | 8/2001 | Neukermans | B82Y 35/00 73/105 |

(Continued)

FOREIGN PATENT DOCUMENTS

WO    WO1997045862    12/1997

*Primary Examiner* — Michael A Lyons
(74) *Attorney, Agent, or Firm* — TransPacific Law Group; Pavel I. Pogodin, Esq.

(57) ABSTRACT

An apparatus for in-line testing and surface analysis of a sample contains a base which stationarily supports a column and moveably supports an optical microscope, an interferometer, and at least test unit such as a scratch and abrasive wear tester that are moveable on the column in the Z-axis direction. A sample secured on a sample table, which is supported by a replaceable tribology drive unit on an X-stage that may position the sample under the microscope, interferometer, or test unit. Depending on the type of the test, the replaceable tribology unit may impart to the sample either a linear reciprocating movement or a rotating movement. The apparatus may operate in an automatic mode and is provided with a central processing unit that control movements of all moveable units through respective drivers via controllers connected to the central processing unit.

14 Claims, 7 Drawing Sheets

(56) References Cited

U.S. PATENT DOCUMENTS

| | | | | |
|---|---|---|---|---|
| 7,489,407 B2* | 2/2009 | Hill | ............... | G03F 7/70775 |
| | | | | 356/508 |
| 7,978,346 B1* | 7/2011 | Riza | ............... | G01B 11/24 |
| | | | | 356/368 |
| 8,353,060 B2* | 1/2013 | Watanabe | ............ | G01Q 10/04 |
| | | | | 250/306 |
| 8,742,344 B2* | 6/2014 | Hatakeyama | ......... | H01J 37/28 |
| | | | | 250/306 |
| 8,902,431 B2* | 12/2014 | Liesener | ............ | G01B 11/2441 |
| | | | | 356/479 |
| 2003/0052495 A1 | 3/2003 | Casarotti et al. | | |
| 2004/0075288 A1 | 4/2004 | Baker | | |
| 2006/0157998 A1 | 7/2006 | Gershenzon et al. | | |
| 2006/0163480 A1* | 7/2006 | Koyama | ............. | G01R 31/311 |
| | | | | 250/310 |
| 2013/0056635 A1* | 3/2013 | Kimba | ............... | H01J 37/28 |
| | | | | 250/310 |
| 2013/0147939 A1* | 6/2013 | Nawata | ............... | A61B 5/00 |
| | | | | 348/79 |
| 2014/0158885 A1* | 6/2014 | Noji | ............... | G01N 23/225 |
| | | | | 250/307 |
| 2014/0312227 A1* | 10/2014 | Yoshikawa | ........ | G01N 23/2204 |
| | | | | 250/310 |
| 2015/0097116 A1* | 4/2015 | Hatakeyama | ......... | H01J 37/28 |
| | | | | 250/310 |
| 2015/0206704 A1* | 7/2015 | Momoi | ............... | G02B 21/26 |
| | | | | 250/310 |
| 2015/0287570 A1* | 10/2015 | Hayashi | ............ | H01J 37/222 |
| | | | | 250/310 |
| 2017/0067735 A1* | 3/2017 | Khosla | ............. | G01N 19/00 |

* cited by examiner

APPARATUS FOR IN-LINE TESTING AND SURFACE ANALYSIS ON A MECHANICAL PROPERTY TESTER

FIELD OF THE INVENTION

The present invention relates to the field of testing materials and more particularly to an apparatus for in-line testing and surface analysis on a mechanical property tester. More specifically, the invention relates to an apparatus and a method for in-line surface analysis on a mechanical tester, with multiple sequential measurements of the test surface by means of a microscope, interferometer, profilometer, scatterometer, or another surface-condition analyzing tool. The invention may find use in tribology and wear and scratch testing.

During a tribology test, the engaging surfaces of two samples are brought in contact to measure friction and wear. In a reciprocating, rotary, fretting, or oscillating test, one of the samples may move while the other sample remains stationary. In some cases, the upper sample may be stationary while in other cases the upper sample may be moveable. The test requires applying a known force and studying the effects of force, speed, time, temperature, or other factors of friction, wear, life of coatings or bulk materials, lubricants, fluids, etc. In tribology, important parameters are load, stroke, speed, and environmental conditions.

A variety of methods and apparatuses can be used for measuring and analyzing the results of tribology tests. Such methods and apparatuses can be classified as mechanical, electrical, and optical. Each of these groups offers different implementation. For example, a scratch test measures the adhesion or hardness of coating or matrix materials. Typically, such a test involves moving a sharp tip for a fixed distance at a known velocity under an increasing or constant load. The final scratch marks are analyzed (during and after test) to calculate adhesion or hardness of the material. Such methods and apparatus are available in a variety of modifications, one of which is a tester coupled with an atomic force microscope.

For example, US Patent Application Publication 2015/0075264 issued in 2015 discloses an optical microscope used for pre-inspection of a subject, wherein an atomic force microscope (AFM) integrated with the optical microscope is passed over a subject and the subject surface is scanned according to the measured deflection of the AFM cantilever. A laser is directed at the cantilever, and the reflected laser light is incident on a photodiode that accordingly detects deflection of the cantilever. The AFM cantilever deflects according to one of the mechanical contact forces, van der Waals force, capillary forced, chemical bonding, electrostatic force, magnetic force, etc.

One of the advanced methods in the field of material testing is the use of confocal microscopy (see. e.g., U.S. Pat. No. 7,839,496 issued on Nov. 23, 2010 to Leonard J. Borucki). The invention relates to a sample holder for confocal microscopy of chemical mechanical polishing (CMP) pad samples cut or otherwise removed from either new or used CMP pads that maintains uniform load and pressure over the part of the sample visible to the confocal microscope.

U.S. Pat. No. 5,760,950 issued on Jun. 2, 1998 to Maly, et al, discloses a scanning confocal microscope optical system for forming an image of a subject illuminated by light from an illumination system that includes a Nipkow disk arranged perpendicular to a light propagation path and that has a surface on which a plurality of pinholes are distributed substantially symmetrically about an axis perpendicular to the surface of the disk. The system further includes components for projecting an image of a first set of pinholes onto a second set of pinholes, the image being formed of light transmitted by the first set of pinholes when the first set is illuminated by light that impinges on the first side of the disk. The system further includes a collective lens and a first objective lens for focusing light transmitted by the second set of pinholes onto the subject and for collecting light reflected by the subject. The first objective lens has a large numerical aperture. Light reflected by the subject passes through the second set of pinholes. Finally, the system may include a device for spinning the Nipkow disk about the axis.

Chinese Patent No. 102607977 B issued in 2014 describes an abrasion in-situ measuring device and a method based on digital image processing. This device comprises an attachment to a universal material tester and contains a frame attachable to the base of the tester and supporting sliders moveable in the directions of X, Y, and Z axes, one slider of which carries a digital microscope that can be used for recording the results of testing in situ and for subsequent analysis of the recorded data.

However, the device of the type described above has disadvantages such as positional inaccuracy after attachment/dismantling; nonrepeatability of measurement point position at multiple measurements of the same sample in the course of a single test cycle, a complex structure, low compactness, etc.

Also known in the art are various interferometers such as a Fabry-Pérot and Nomarsky. An interferometer suitable for tribology is the Nexview™ 3D Optical Surface Profiler of Zygo®, CT, USA. This interferometer is capable of measuring any surface—from super smooth to very rough, with subnanometer precision.

The interferometer includes an automated 200-mm Integrated Measurement Stage. In tribology this instrument is used, e.g., for 3D measurements and for inspection of surface roughness, in particular, for inspection of properties such as height of micro roughness and surface nonuniformity.

SUMMARY OF THE INVENTION

The apparatus of the invention for in-line testing and surface analysis of a sample on a mechanical property tester contains a base that supports a column in a stationary manner and moveably supports an X-stage with a drive unit for moving the X-stage on the base in the direction of the X-axis. The X-stage, in turn, supports a tribology drive unit with a replaceable drive that may reproduce linear reciprocation of the sample in the X-axis or Y-axis direction or rotation of a sample table that supports a sample to be tested. The column moveably supports at least two units, one being an optical microscope and the other being a test unit that may function as a hardness tester, or alternatively, the column may additionally support a second test unit, e.g., a scratch or abrasive wear tester, and a microscope in combination with an interferometer for 3D measurements. In all cases, the sample holding unit moves along a line that is oriented in the X-axis direction and may be aligned with the position of the working field of the optical microscope so that after each test the sample can be repeatedly positioned in the working field of the optical microscope and/or interferometer without removal from the sample table supported by the tribology drive unit on the X-stage. The Y-axis movement of the tribology drive unit may be used for presetting the position of the sample relative to the optical instrument or interferometer before multiple and repeated movement of the X-stage in the X-axis direction. Such an arrangement makes it possible to provide compact construction, reliably positioning the sample in the same place for repeated measurements to observe the dynamics of changes on the surface of the sample and to improve repeatability and accuracy of the measurement results. Alternately, the apparatus of the invention may combine a confocal microscope with an interferometer since the confocal microscope allows observation of the sample surface, while the interferometer allows 3D measurements of the surface structural elements, such as micro roughness caused by, e.g., an abrasion test. Precise positioning of the sample at the same point during multiple, repeated observations and measurements is provided by installing the tribology drive unit on a layered piezoelectric drive package that is equipped with X,Y,Z microdrives for scanning movements of a small portion of the sample surface relative to an optical beam of the interferometer.

DETAILED DESCRIPTION OF THE INVENTION

Based on their test results, the inventors herein showed that mechanical property test results depend on the surface morphology of test samples. Surface parameters such as surface roughness, texture, tilt, etc., may significantly affect final test data (friction, wear, hardness, adhesion, etc). The inventors herein concluded that multiple surface parameter information obtained exactly at the point of test can help tremendously to obtain correct test results.

Also, after test completion, important post-test parameters such as volume wear, roughness change, crack propagation, etc., may be needed to perform test-data analysis. Currently, samples are removed from the mechanical tester and are then taken to different surface measurement instruments for pre-test and post-test measurements.

The present invention comprises an apparatus that integrally combines a material test unit with a sample measurement and analysis system installed on and sharing a common base; and a Y-stage, X-stage, and common column for supporting at least two individual Z-stages, one for the test unit and one for the measurement unit. Such an arrangement makes it possible to provide compact construction, to reliably position a sample at the same location in case of repeated measurements for observing the dynamics of surface changes on the sample, and to improve repeatability and accuracy of measurement results.

Figure 1:
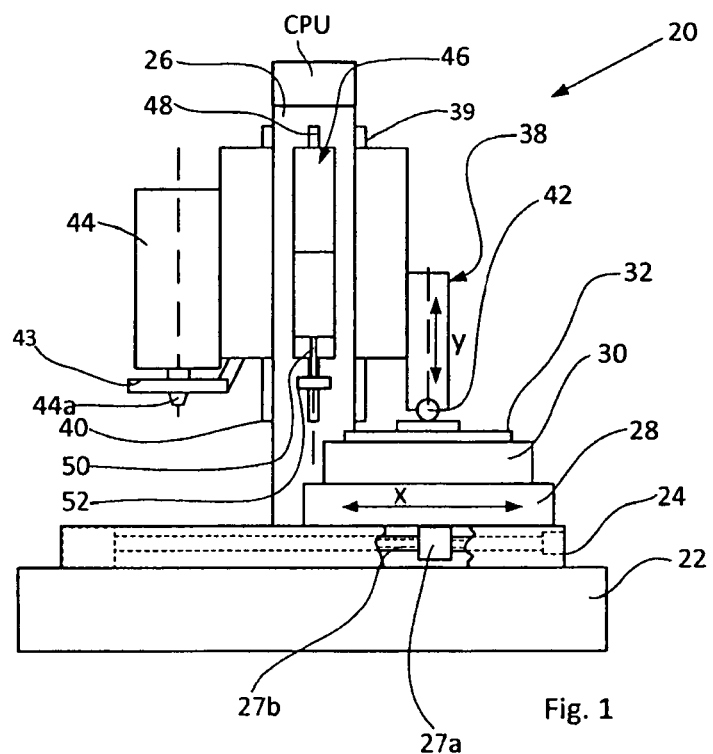
FIG. 1 is a schematic view of the apparatus of the present invention in one of the test stages.

The apparatus of the invention is designated by reference numeral 20 and is schematically shown in FIG. 1, which is a side view of the apparatus shown in one of the test stages.

The apparatus 20 comprises a base 22 that supports Y-stage 24, which is moveable in the direction of the Y-axis and perpendicular to the plane of the drawings (see FIGS. 3a and 3b, which are explained later). The base 22 (stationary) supports a column 26, which extends vertically from the base 22. The Y-stage 24 (moveable) supports an X-stage 28, which is moveable in the X-axis direction, e.g., with the use of a first X-axis drive means, such as a lead-and-nut drive mechanism. As shown in FIG. 1, a nut 27 can be attached to the X-stage 28 and engages a lead screw 27b driven into rotation by a motor 29. The X-stage 28 supports a tribology drive unit 30, which, in turn, supports a sample stage 32.

The above-described systems with two standard motorized stages moveable in X and Y directions are well known and commercially available, e.g., from GMT Global Inc. Each X-Y stage is a standard unit of CXN and CXC series with table sizes from 50×50 mm to 80×80 mm. The travel length for the stages may reach 420 mm. The drive is performed from a motor through a precise ball screw shaft of the C5 level of accuracy. The commercially available X-Y system mentioned above is given only as an example; many other similar systems can be used for the purposes of the invention. All the X-Y stages are equipped with respective stepping motors or servomotor drivers, which are controlled from a central processing unit (CPU).

Figure 2A:
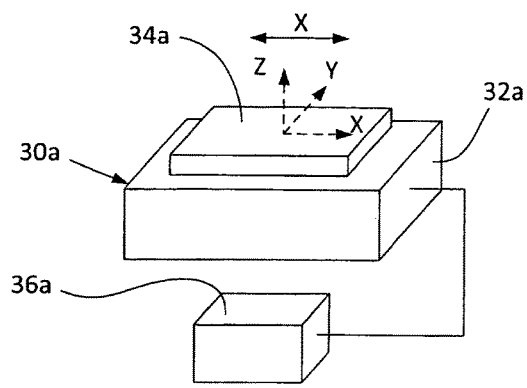
FIG. 2a is a three-dimensional view of the tribology drive used in the apparatus of the invention, with a sample table for tests that involve reciprocating movements of the sample.
Figure 2B:
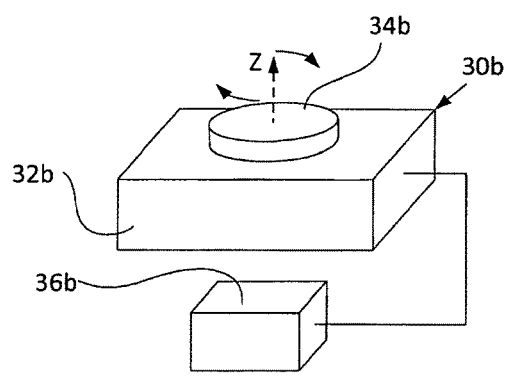
FIG. 2b is a three-dimensional view of the tribology drive used in the apparatus of the invention, with a sample table for tests that involve rotational movements of the sample.

The tribology drive 30 comprises an interchangeable unit that may be driven either from a reciprocating linear drive in the X-axis direction or from a rotary drive (see FIGS. 2A and 2B).

Figure 2C:
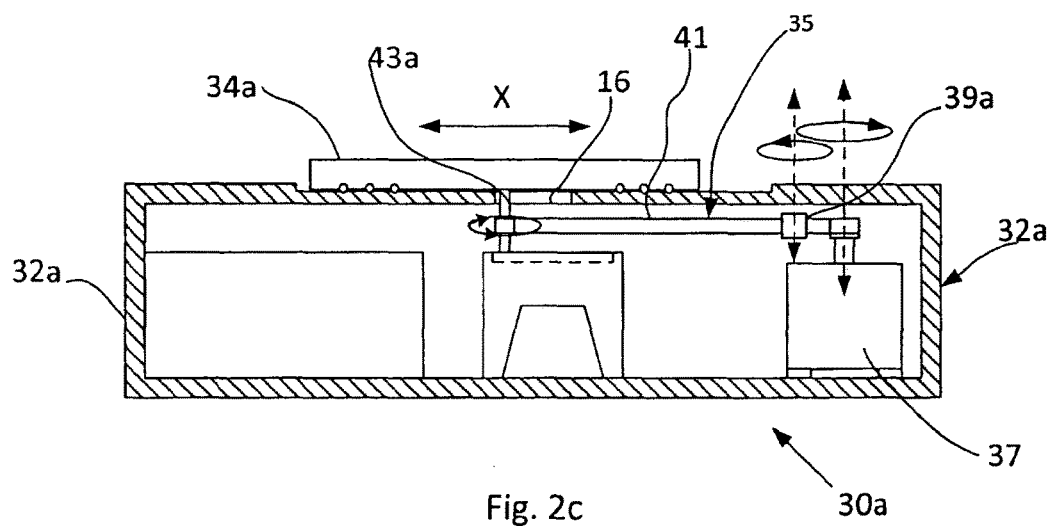
FIG. 2c is a sectional view of the tribology drive base, illustrating an example of a reciprocating mechanism for reciprocation of the sample table during scratch or wearability testing.

FIG. 2a shows an interchangeable tribology unit 30a that comprises a tribology drive base 32a that can be interchangeably secured to the X-stage 28 (FIG. 1). The tribology drive base 32a, in turn, supports a sample table 34a that can be driven reciprocatingly in the X-axis direction. The sample table 34a is used for securing and holding a specimen to be tested (not shown in FIG. 2a) that can be pasted to the sample table 34a or otherwise secured before testing. The reciprocating movements in the X-axis direction are performed, e.g., with the use of a crank-and-rod mechanism 35 of the type shown in FIG. 2c. The mechanism 35 is located in the tribology drive base 32a and consists of a motor 37 that rotates a crank 39a pivotally connected with a rod 41 which, in turn, is pivotally connected to a slider 43a that slides in the slot 45 and is connected to the bottom of the sample table 34a.

Reference numeral 36a(FIG. 2a) designates a controller that controls operation of a drive motor 37. The controller 36a is controlled from a CPU (FIG. 1).

FIG. 2b shows an interchangeable tribology unit 30b that comprises a tribology drive base 32b that can be interchangeably secured to the X-stage 28 (FIG. 1). The tribology drive base 32b, in turn, supports a sample table 34b that can be driven into rotation around a vertical axis Z.

Figure 2D:
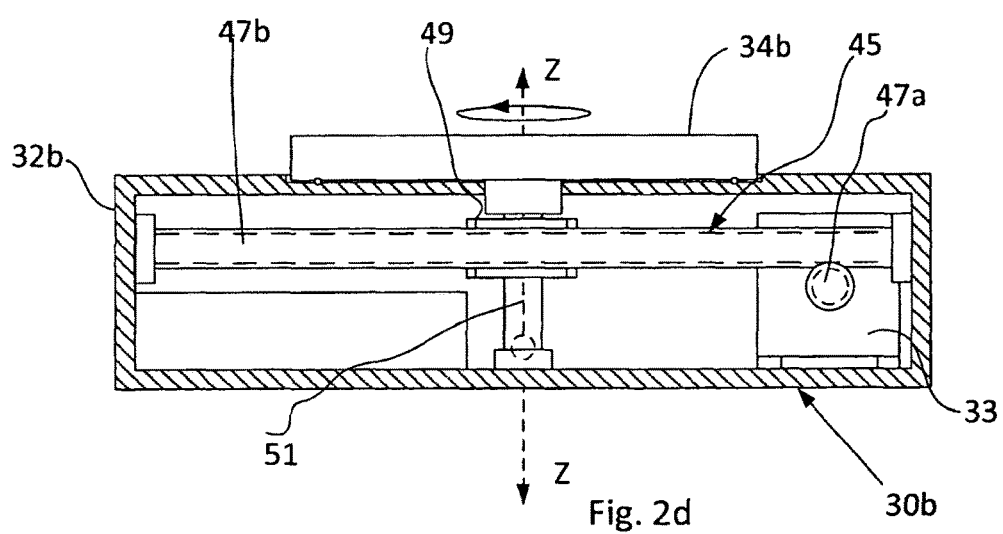
FIG. 2d is a sectional view of the tribology drive base, illustrating an example of a rotary mechanism for rotation of the sample table during scratch or wearability testing.

An example of a mechanism 45 for rotation of a sample table 34b is shown in FIG. 2d. The mechanism is located in the tribology drive base 32b and comprises a drive motor 33, the output shaft of which supports a gear 47a wheel that engages a worm 47b, which, in turn, engages another gear wheel 49. The gear wheel 49 is secured on a shaft 51, which is oriented in the Z-axis direction and supports on its top the sample table 34b of a rotary-type interchangeable tribology unit 30b.

The sample table 34b is used for securing and holding a sample or specimen to be tested (not shown in FIGS. 2b and 2d) that can be pasted to the sample table 34b or otherwise secured during testing. Reference numeral 36b designates a controller that controls operation of a rotary drive motor 33 which is located in the tribology drive base 32a and imparts rotary motions to the sample stage 34b. The controller 36b is controlled from the CPU.

CPU controllable tester motions mentioned above for tribology drives 30a and 30b are exemplified by motions of lower drives on commercially available tribology testers produced by a number of manufacturers.

For example, American Electric Power Technology (USA) offers the tribology tester UT-3000 with various, easily interchangeable lower drives such as rotary, fast reciprocating, block on ring, linear drive, etc., to replicate any motion. Choice of the drive is dictated by the test required, such as scratch test that uses a linear drive, fretting test that uses a fast reciprocating drive, or a pin on disk test that uses a rotary drive, and so on. All of these drives are independently programmable, and their interrelationships will be described later with reference to FIG. 4.

Bruker Company offers a Universal Mechanical Tester (UMT) that offers a wide range of interchangeable drives and fixtures for testing samples under multiple different wear patterns on a single test platform. The UMT offers users infinite combinations of synchronized motion control for both upper and lower samples. The upper sample can be translated along any axis or rotated. Motion can occur either unidirectionally or in a programmed combination of axes and speeds. The lower sample has a wide range of available motion control. Linear translation is available in X and Y axes, as well as fast reciprocating linear motion for fretting and wear tests. Changeover from reciprocating to rotary motion takes just a few minutes, and the lower sample can be rotated along the vertical axis (pin-on-disk) or horizontal axis (block-on-ring).

A unique feature of the apparatus 20 of the invention for in-line test and surface analysis is a combination of a Z-axis test unit, or at least two Z-axis test units, which are installed on a common vertical column, with a measurement unit, e.g., a microscope, and/or interferometer, wherein the microscope and/or interferometer and the Z-axis test unit or units are arranged on the same line oriented in the X-axis direction, secured on the common column with possibility of adjustable positioning in the Z-axis direction, and located exactly above the trajectory of movement of the sample carried by the X-stage in the X-axis direction so that after each test the sample can be repeatedly placed into the same position for optical analysis without removal from the sample table. Such an arrangement makes it possible to provide compact construction, to reliably position the sample at the same place in case of repeated measurements for observing dynamics of changes on the surface of the sample, and to improve repeatability and accuracy of measurement results.

More specifically, as shown in FIG. 1, the column 26 supports at least one Z-stage, such as a first Z-stage test unit or a test unit 38, e.g., a hardness measurement unit moveable in the Z-axis direction. The first Z-stage test unit 38 is adjustably moveable in the direction of the Z-axis along guides 39, e.g., from a rack-and-wheel mechanism (not shown).

An example of a hardness tester 38 that can be installed on the column 26 is the EZ-X Series Tabletop Electromechanical Universal Tester of Simadzu Co., Japan. This tester has a capacity up to 500 N. It is equipped with high-performance load cells with accuracy of ±0.5% or ±1% of the indicated force value. The EZ-X series can be connected with the CPU of the testing machine 20 and provides objective numerical test results that can supplement analysis data. The hardness tester 38 makes it possible to test hardness by various methods such as Brinell, Vickers, Rockwell, etc.

The test probe 42, which is shown as a Brinell hardness spherical probe, is intended to interact with a sample (not shown), which is installed on the sample table 34a (FIG. 2a) which in this case is fixed in the stationary position and aligns the sample with the hardness probe (FIG. 1). The tribology drive base 32a should possess rigidity sufficient to resist the force developed by the force cell of the hardness tester 38.

Installed on the same column 26 in its own guides 40 is a microscope 44, which is intended for observation and optically recording results of the sample tests. These results are transmitted to the CPU (FIG. 1). In the illustrated case of the hardness tester 38, the microscope 40 measures the indent obtained as a result of impression of the probe 42 into the specimen. According to conventional practice, the analysis sent to the CPU considers the diameter of the indented part, indenting time, time of retention under maximum load, maximum load, etc.

After the sample testing operation on the tribology drive 30 is over, the test unit 38 is lifted, and the entire X-stage 28 is moved by the X-stage drive, such as a lead screw and nut mechanism (27a, 27b) to the position aligned with the objective lens 44a of the microscope 44 where observation and recording of the observation analysis can be performed in accordance with conventional practice. The position of the apparatus units is shown in FIG. 3b.

It is understood that the Brinell tester with the spherical indenter 42 is shown only as an example, and the indenter may have a pyramid shape for measuring hardness on a Vickers scale, or the like.

A great variety of microscopes is available for the purposes of the invention. Most suitable is an optical digital microscope with a bright field for microscopy associated with digital imaging, a wide range of working distances, and possibilities for adjusting positions and incidence angles of light beams, etc. Reference numeral 43 (FIG. 1) designates a microscope illumination system that can be adjusted to a position most optimal for illumination of a specific specimen surface.

If necessary, the column 26 may support a second Z-stage test unit 46, the position of which can be adjusted in its own vertical guides 48. The test unit 46 is provided with a tool/specimen holder 50 in which an upper stationary member 52 (FIG. 1), such as an upper sample, scratching tool, etc., can be secured relative to the moveable sample 53 (FIG. 3b) fixed on the surface of the tribology drive unit 30 for frictional interaction with the upper stationary member 52. For the tribology drive 30a, the upper stationary member 52 will interact with the sample 53 that performs reciprocating movement in a scratch or abrasive wear test; for the tribology drive 30b the upper stationary member will interact with the rotating sample used for the same purposes as in the reciprocating test.

It is understood that the second Z-stage test unit 46 is equipped with a force measurement cell (not shown) that is connected to the CPU for processing the results of the tests obtained on this unit and for combining the obtained data with the data from other units in the final analysis of the sample characteristics. Such devices are known in the art.

Operation of the apparatus 20 of the invention for in-line testing and surface analysis is described below with reference to FIGS. 3a, 3b, and 3c which are side views of the apparatus in different operational positions during the test of the same sample which until the end of the test remains secured on the sample table of the tribology drive 30, 30a, or 30b.

FIG. 1 shows an arrangement of the units of the apparatus 20 at which the sample 53 is located under the probe 42 during the hardness test, e.g., Brinell hardness test. In this operation, the sample installed on the tribology drive 30 is located directly under the first Z-station test unit and is aligned with its probe 42. Such a position is used, e.g., for measuring hardness of the sample 53. This situation corresponds to FIG. 3c.

Figures 3A, 3B, 3C:
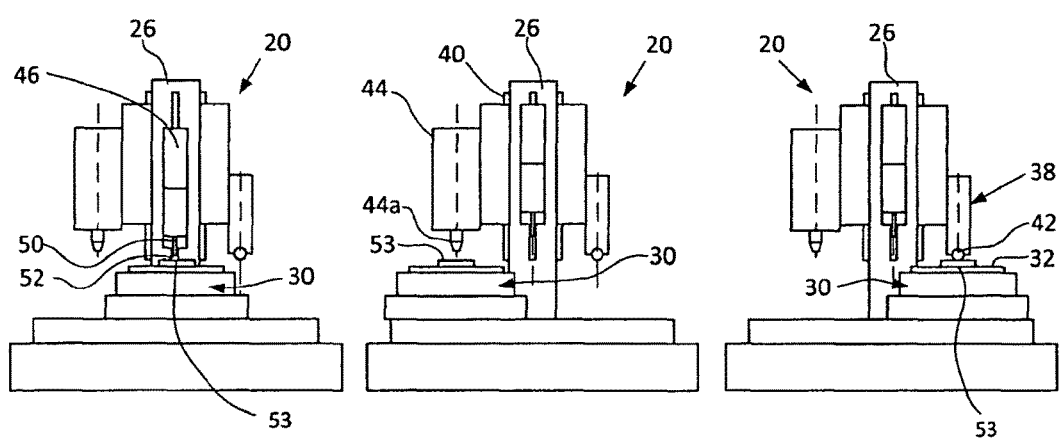
FIG. 3a is a side view of the apparatus of the invention in a position for conducting a scratch or abrasive wear test, with a sample reciprocating relative to a stationary tool installed on the column.
FIG. 3b is a side view of the apparatus of the invention in a position in which the tested sample is located in the microscope working field.
FIG. 3c is a side view of the apparatus of the invention in a position similar to that shown in FIG. 1, wherein the sample is located under the first Z-stage test unit for measuring, e.g., hardness of the material.

FIG. 3a shows an arrangement of the units wherein the sample 53 is located under the upper stationary member 50 during the scratching or abrasive wear test. In this operation, the sample 53 installed on the tribology drive 30a or 30b is located directly under the second Z-station test unit 46 and is aligned with the upper stationary member 52. Such a position is used, e.g., for the scratching or abrasion wear test in which the stationary upper member 52 interacts with a reciprocating or rotating sample, respectively.

FIG. 3b shows an arrangement of the units wherein the sample 53 is located under the objective 44a of the microscope 44 and with its surface within working distance from the microscope objective 44a.

Figure 4:
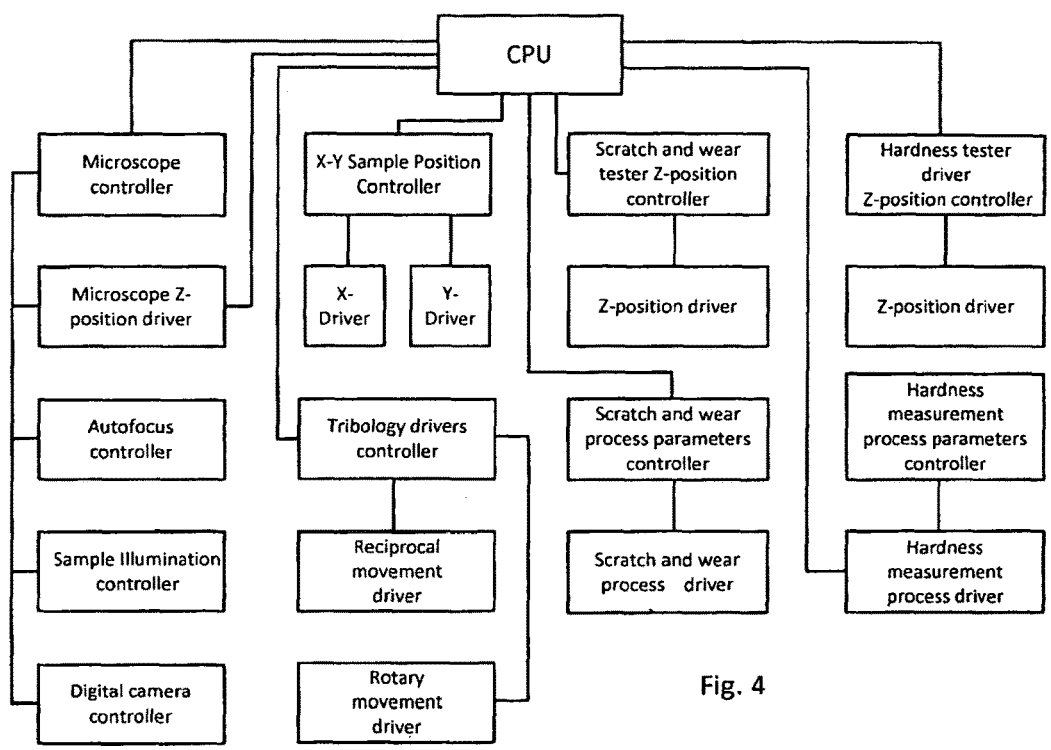
FIG. 4 is a block diagram of control units of the apparatus of the invention.

FIG. 4 is a block diagram of a control system of the apparatus of the invention. In this control system, all signals from sensors that detect positions of the parts and units of the apparatus moveable during the test and in a position ready for testing, as well conditions that can be changed during the test, are collected and processed in the CPU. The aforementioned sensors are not shown since they are well known in the art and are used in any conventional tester with automatic control. Some control components shown in FIG. 4, such as controllers, are grouped on a control board (not shown) and are electrically connected to respective drivers that, in turn, control operations of the actuating members, such as motors. The main controllers that may be located on the control board are the following: microscope controller, X-Y sample position controller, scratch and wear tester Z-position controller, and a hardness tester Z-position controller. The drivers connected to the respective controllers are normally located near or on the respective actuating members. These are the microscope Z-position driver, X-axis driver, Y-axis driver, Z-axis driver, etc.

Figure 5:
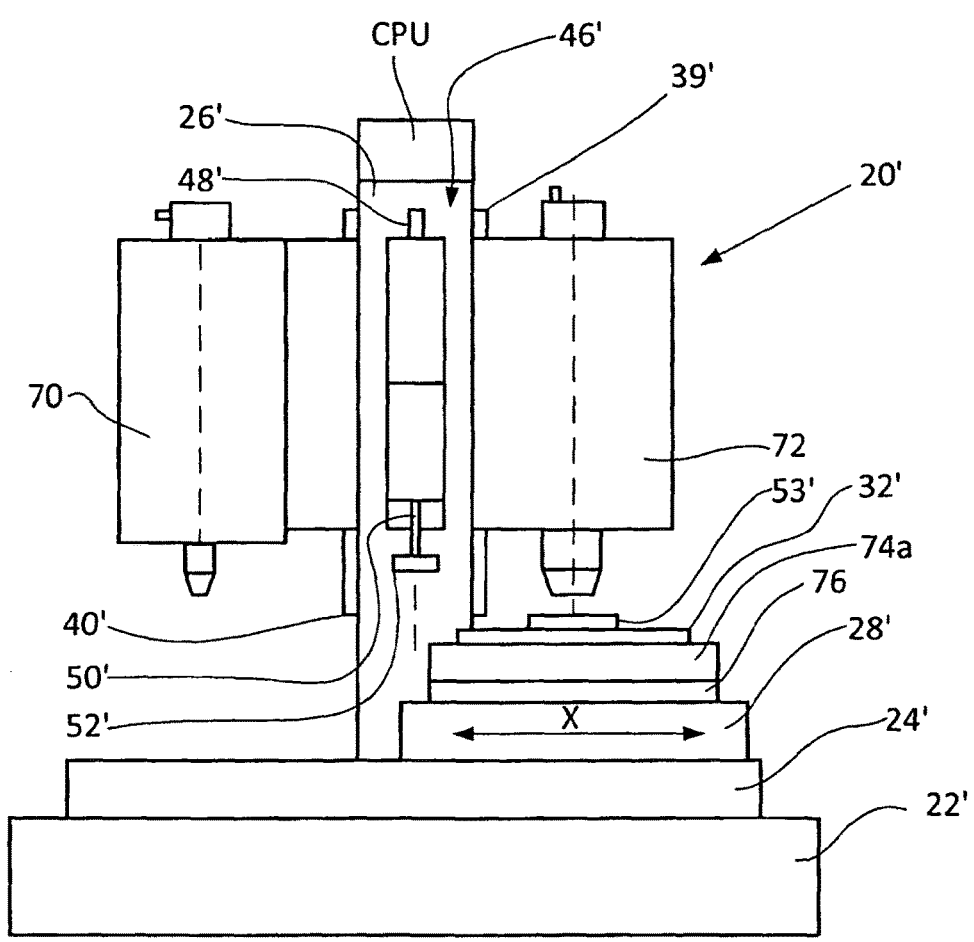
FIG. 5 is a view similar to FIG. 1 but showing the use of a microscope in combination with an interferometer installed on the common column.
Figures 6A, 6B:
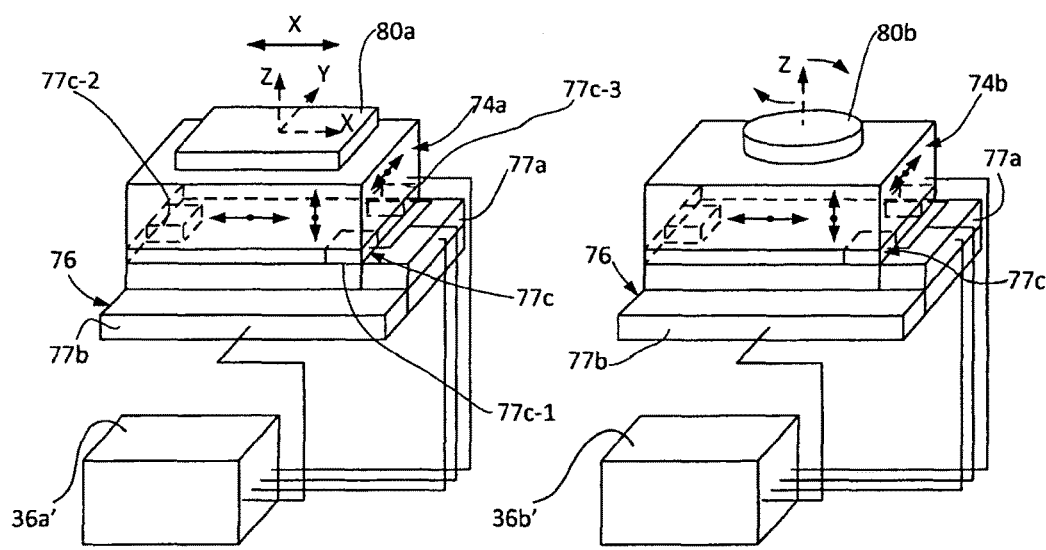
FIG. 6a is a view similar to FIG. 2a, illustrating a modification in which the tribology drive unit is installed on a layered piezoelectric drive package that is equipped with X,Y,Z microdrives for imparting to the tribology drive unit, and, hence, to the sample, scanning displacements in the X, Y, and Z axes directions relative to the beam emitted from the microscope or from the interferometer during surface analysis of the sample that has undergone testing with linear movements of the sample.
FIG. 6b is a view similar to FIG. 6a, except that the sample is analyzed after passing a test with rotary movements.

FIGS. 5, 6a, and 6b illustrate another modification of the apparatus, wherein FIG. 5 is a view similar to FIG. 1 but shows the use of a microscope 70 in combination with an interferometer 72 installed on the common column 46'.

FIG. 6a is a view similar to FIG. 2a, illustrating a modification in which the tribology drive unit 74a is installed on a layered piezoelectric drive package 76 that is equipped with X,Y,Z microdrives for imparting to the tribology drive unit, and, hence, to the sample, scanning displacements in the X, Y, and Z directions relative to the beam emitted from the microscope 70 or from the interferometer 72 during surface analysis of the sample that has undergone testing with linear movements of the sample.

FIG. 6b is a view similar to FIG. 6a, except that the sample is analyzed after passing a test with rotary movements.

In FIGS. 5, 6a, and 6b, the parts that are identical with those shown in FIGS. 1 to 4 are omitted from the description and are designated by the same reference numeral with an addition of a prime. Thus, the base 22 is shown as the base 22', the column 26 is designated as 26', etc.

As shown in the above-named drawings, the apparatus of the invention combines the laser scanning reflective confocal microscope 70 with the interferometer 72.

Such microscopes are commercially available on the market. An example is LT-9000 series Surface Scanning Laser Confocal Displacement Meter that can be purchased from Keyence, Il, USA. This device provides two-directional scanning for accuracy and stability. It combines a tuning fork and oscillating unit for using a surface-scanning laser. This allows advanced displacement and profile measurements that are unaffected by target color or angle. The microscope of LT-9000 type produces Z-axis scanning by combining a tuning fork with the confocal principle. X-axis scanning is provided by installing the tribology drive unit 74a (for linear movements) or 74b (for rotary movements) on a layered piezoelectric drive package 76 that is equipped with X,Y,Z microdrivers which are sandwiched into a layered structure for performing scanning micro displacements relative to the beam emitted from the laser scanning reflective confocal microscope 70 (FIG. 5). Here, reference numeral 77a designates an X-axis microdriver, reference numeral 77b designates a Y-axis microdriver, and reference numeral 77c designates a Z-axis microdriver.

The Z-axis microdriver 77c consists of three subunits 77c-1, 77c-2 and 77c-3 on which the tribology drive unit 74a (in case of linearly tested sample) or the tribology drive unit 74b (in case of rotary tested sample) rests.

As a result, the beam may scan a small portion of the surface of the sample (not shown) supported by the sample table 80a (or 80b) installed on the tribology drive unit 74a (or 74b) in X, Y, or Z directions.

The layered piezoelectric drive package 76 with X, Y microdrives is commercially available, e.g., from ThorLabs, NJ, USA. Such units comprise Amplified Piezoelectric Actuators, 220 µm to 420 µm travel and are made in the form of 75-V Low Voltage Piezo Stacks, which develop displacement force up to 100 N with the stroke length of 220 μm or 420 μm.

Each Z-axis direction microdriver 77c-1, 77c-2, and 77c-3 is known and commercially available, e.g., from Physik Instrumente, Germany. For example, each Z-axis microdrive comprises a P-601 Motion-Amplified Piezo Flexure Z-Actuator which is a Flexure Guidance for Frictionless, Ultra-Straight Motion. This actuator has a travel ranges to 480 μm and resolution to 0.2 nm.

By coordinating the results of precise 3D measurements of the elements of surface topology made by an interferometer with the results of measurements obtained from a confocal reflective laser microscope, it becomes possible to install the selected portion of the sample surface at the same point during multiple, repeated measurements performed during the test without removing the sample from the sample table. Such periodic measurements on the same sample and in the same place of the sample surface are needed for observing and recording the dynamics of surface changes, e.g., under the effect of scratching or abrasion. Such results are possible only when a microscope and interferometer provided with a surface microscanning function are used as an indispensable combination. Another unique feature is that the aforementioned micro displacements are performed by the sample table installed on a tribology table moveable with scanning motions relative to the stationary measuring optical beam.

Although the invention is shown and described with reference to specific embodiments, it is understood that these embodiments should not be construed as limiting the areas of application of the invention and that any changes and modifications are possible, provided these changes and modifications do not depart from the scope of the attached patent claims. For example, test units other than the hardness tester, scratch tester, or abrasive wear tester can be installed on the column 26. Drives different from the screw-and-nut type can be used for moving the X-stage. The test units may be located on the left side of the column, and the microscope may be installed on the right side of the column.

The invention claimed is:

1. An apparatus for in-line testing and surface analysis of a sample on a mechanical property tester comprising:
   a base in an X-Y plane having mutually perpendicular X-axis and Y-axis;
   an Y-axis stage having a first Y-axis drive means for moving the Y-stage in the direction of the Y-axis;
   an X-axis stage supported by the Y-axis stage and having a first X-axis drive means for moving the X-stage in the direction of the X-axis;
   a sample carrying unit for carrying a sample supported by the X-axis stage;
   a stationary column fixed to the base and oriented in the direction of Z-axis perpendicular to the X-Y plane;
   at least one sample test unit installed on the stationary column and having a first Z-axis drive means for moving the at least one sample test unit in the direction of the Z-axis along the stationary column;
   an optical measurement unit having a working field and a second Z-axis drive means for moving the optical measurement unit in the direction of the Z-axis along the stationary column;
   an interferometer that emits an optical beam and is installed on the stationary column and having a third Z-axis drive means, wherein the at least one sample test unit, the optical measurement unit, and the interferometer are arranged on the same line oriented in the X-axis direction and are located in an aligned position relative to the movement of the test sample carried by the sample carrying unit supported by the X-axis stage so that after each test of the sample with the at least one sample test unit, the sample can be repeatedly positioned in the working field of the optical measurement unit without removal from the sample carrying unit; and a central processing unit for controlling movements of the at least one sample test unit, optical measurement unit, and the sample carrying unit.

2. The apparatus of claim 1, wherein the optical measurement unit comprises a laser scanning reflective confocal microscope, and the interferometer comprises a 3D measurement interferometer.

3. The apparatus of claim 2, wherein the sample carrying unit for carrying a sample to be tested on a sample stage comprises a set of interchangeable tribology drive units, one of which has a reciprocating drive means for reciprocating a sample table with the sample in the directions of at least axis X or axis Y and another of which has a rotary drive means for rotating the sample table with the sample.

4. The apparatus of claim 3, wherein at least one sample test unit is a scratching and abrasive wear test unit that interacts with the sample when the sample performs reciprocating or rotating movements by means of said interchangeable tribology drive units.

5. The apparatus of claim 3, wherein the first X-axis drive means is a lead screw installed in the Y-axis stage and a nut engageable with the lead screw installed in the X-axis stage.

6. The apparatus of claim 5, wherein the reciprocating drive means comprises a crankshaft mechanism, and the rotary drive means comprises a rotary motor.

7. The apparatus of claim 6, further comprising a layered piezoelectric drive package having an X-axis microdrive supported by the X-axis stage, an Y-axis microdrive supported by the X-axis microdrive, and a Z-axis microdrive supported by the Y-axis microdrive, the interchangeable tribology drive units of said set being supported by the Z-axis microdrive, wherein the X-axis microdrive, Y-axis microdrive, and Z-axis microdrive perform scanning micro movements of the sample supported by the sample table relative to the optical beam of the interferometer.

8. The apparatus of claim 1, wherein the sample carrying unit for carrying a sample to be tested on a sample stage comprises a set of interchangeable tribology drive units, one of which has a reciprocating drive means for reciprocating a sample table with the sample in the directions of at least axis X or axis Y and another of which has a rotary drive means for rotating the sample table with the sample.

9. The apparatus of claim 8, wherein the first X-axis drive means is a lead screw installed in the Y-axis stage and a nut engageable with the lead screw installed in the X-axis stage.

10. The apparatus of claim 9, wherein the reciprocating drive means comprises a crankshaft mechanism, and the rotary drive means comprises a rotary motor.

11. The apparatus of claim 8, further comprising a layered piezoelectric drive package having an X-axis microdrive supported by the X-axis stage, an Y-axis microdrive supported by the X-axis microdrive, and a Z-axis microdrive supported by the Y-axis microdrive, the interchangeable tribology drive units of said set being supported by the Z-axis microdrive, wherein the X-axis microdrive, Y-axis microdrive, and Z-axis microdrive perform scanning micro movements of the sample supported by the sample table relative to a laser beam of the interferometer.

12. The apparatus of claim 1, wherein the sample carrying unit for carrying a sample to be tested on a sample stage comprises a set of interchangeable tribology drive units, one of which has a reciprocating drive means for reciprocating a sample table with the sample in the directions of at least axis X or axis Y and another of which has a rotary drive means.

13. The apparatus of claim 12, wherein the first X-axis drive means is a lead screw installed in the Y-axis stage and a nut engageable with the lead screw installed in the X-axis stage.

14. The apparatus of claim 13, wherein the reciprocating drive means comprises a crankshaft mechanism, and the rotary drive means comprises a rotary motor.

* * * * *